United States Patent [19]

Bott et al.

[11] Patent Number: 4,551,208
[45] Date of Patent: Nov. 5, 1985

[54] RECOVERY OF FORMIC ACID BY DISTILLATION

[75] Inventors: Kaspar Bott, Wachenheim; Gerd Kaibel, Lampertheim; Horst Hartmann, Boehl-Iggelheim; Rudolf Irnich, Bobenheim; Horst Buelow, Frankenthal, all of Fed. Rep. of Germany

[73] Assignee: BASF Aktiengesellschaft, Ludwigshafen, Fed. Rep. of Germany

[21] Appl. No.: 614,280

[22] Filed: May 25, 1984

[30] Foreign Application Priority Data

May 31, 1983 [DE] Fed. Rep. of Germany ....... 3319651

[51] Int. Cl.$^4$ .............................................. B01D 3/34
[52] U.S. Cl. ....................................... 203/60; 562/609; 203/57
[58] Field of Search ............ 203/50, 57, 60, DIG. 21; 562/608, 609

[56] References Cited

U.S. PATENT DOCUMENTS

| | | | |
|---|---|---|---|
| 3,951,755 | 4/1976 | Sartorius et al. | 203/60 |
| 4,217,460 | 8/1980 | Hohenschutz et al. | 562/609 |
| 4,262,140 | 4/1981 | Bott et al. | 562/609 |
| 4,326,073 | 4/1982 | Wolf et al. | 562/609 |

*Primary Examiner*—William F. Smith
*Assistant Examiner*—Andrew J. Anderson
*Attorney, Agent, or Firm*—John H. Shurtleff

[57] ABSTRACT

Formic acid is recovered, by distillation, from its mixtures with solvents of the general formula I

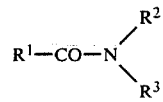

where $R^1$ is hydrogen, methyl, ethyl or vinyl and $R^2$ and $R^3$ are each alkyl, cycloalkyl, aryl or aralkyl, or $R^2$ and $R^3$ together form a 1,4- or 1,5-alkylene group, in each case of not more than 8 carbon atoms, with the provisos that the sum of the number of carbon atoms in $R^2$ and $R^3$ is 7 to 14 and that only one of these radicals is aryl, by a method in which the distillation is carried out in the presence of a carboxamide II which is selected from the group consisting of formamide, acetamide, propionamide and the same compounds substituted by N-methyl or N,N-dimethyl, and which has a boiling point lower than that of the solvent I.

10 Claims, No Drawings

RECOVERY OF FORMIC ACID BY DISTILLATION

The present invention relates to an improved process for the recovery of formic acid, by distillation, from its mixtures with solvents of the general formula I

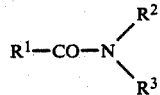

where $R^1$ is hydrogen, methyl, ethyl or vinyl and $R^2$ and $R^3$ are each alkyl, cycloalkyl, aryl or aralkyl, or $R^2$ and $R^3$ together form a 1,4- or 1,5-alkylene group, in each case of not more than 8 carbon atoms, with the provisos that the sum of the number of carbon atoms in $R^2$ and $R^3$ is 7 to 14 and that only one of these radicals is aryl.

Mixtures of this type are obtained in industry when formic acid is extracted from its aqueous solutions using a solvent I; this procedure, followed by distillation of the extract phase, is used for obtaining completely or substantially anhydrous acid cf. U.S. Pat. Nos. 4,217,460; 4,262,140 and 4,326,073 also describe the use of these compounds, especially N-di-n-butylformamide, for the large-scale industrial production of completely or substantially anhydrous formic acid.

All of these processes have in common the fact that they give a mixture of the solvent I and formic acid, with or without some water, and the anhydrous or water-containing acid has to be distilled off from this mixture.

Both in liquid-liquid extraction and in extractive distillation, the extractive action of the solvent I is based in particular on the fact that, depending on the basicity of I, the acid is more or less strongly bonded to I to form a salt, so that the cleavage of these bonds requires additional energy over and above the energy of vaporization of the acid and hence implies additional thermal loading of the material being distilled. When the distillation is carried out under reduced pressure, it is desirable for economic reasons that the pressure should not fall below 40-60 mbar absolute, i.e., so that the space-time yield is not too low and cooling does not have to be carried out to condense the distillate; even in this case, the bottom temperatures have to be about 150°-170° C. in order to separate off the acid completely from I. At these temperatures, however, various undesirable reactions take place, in particular the decomposition of the formic acid.

It is an object of the present invention to design the distillation of the mixtures conforming to the invention in such a way that their thermal loading is reduced without the cost-efficiency of the distillation suffering as a result.

We have found that this object is achieved and that, accordingly, formic acid can be recovered from its mixtures with solvents of the general formula I

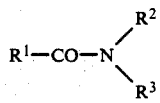

where $R^1$ is hydrogen, methyl, ethyl or vinyl and $R^2$ and $R^3$ are each alkyl, cycloalkyl, aryl or aralkyl, or $R^2$ and $R^3$ together form a 1,4- or 1,5-alkylene group, in each case of not more than 8 carbon atoms, with the provisos that the sum of the number of carbon atoms in $R^2$ and $R^3$ is 7 to 14 and that only one of these radicals is aryl, in an economical and technically advantageous manner by distillation, if the distillation is carried out in the presence of a carboxamide II which has a boiling point lower than that of the solvent I.

Formamides have proven particularly advantageous as the carboxamide II, especially those which are monosubstituted or disubstituted at the nitrogen atom by $C_1$-$C_4$-alkyl, in particular methyl. The corresponding acetamides and propionamides are also suitable, provided they satisfy the boiling point condition in the particular system.

Examples of suitable pairs I and II are shown in the Table below, the boiling points under atmospheric pressure being stated. The relationships essentially also apply under reduced pressure.

TABLE

Suitable pairs of solvent I and carboxamide II for the recovery of formic acid (bp. 101° C.) by distillation.

| Solvent I Type | Bp. °C. | Carboxamide II Type | Bp. °C. |
|---|---|---|---|
| Di-n-butyl-formamide | 247.1 | Formamide | 212.1 |
| | | Methylformamide | 199.3 |
| | | Dimethylformamide | 153.0 |
| | | Acetamide | 222.0 |
| | | N,N—Dimethylacetamide | 165.0 |
| Di-n-pentyl-formamide | about 280 | Formamide | 212.1 |
| | | Methylformamide | 199.3 |
| | | Dimethylformamide | 153.0 |
| | | Acetamide | 222.0 |

The process according to the invention is most important for the extraction of formic acid, using the solvent I as an extracting agent, from those aqueous solutions obtained in the hydrolysis of methyl formate. However, it is not restricted to this, and can therefore also be used for the separation of corresponding mixtures from other sources.

As a general rule, the boiling point of the carboxamide II under atmospheric pressure should be about 20°-80° C. lower than that of the solvent I and about 50°-120° C. higher than that of the formic acid, it being particularly advantageous if the boiling point of II is roughly in the middle of the range from the boiling point of I to that of formic acid. It is also advantageous for the boiling point of I and that of formic acid to differ by not less than 50° C., preferably by 100°-170° C.

Regardless of the amount of acid and of I, the amount of II is advantageously such that, in steady-state operation, II remains predominantly in the middle section of the column, and is not present in large amounts either at the bottom or at the top of the fractionating column. If the bottom fraction and the top fraction nevertheless contain relatively large amounts of II, additional separation operations are advantageous or necessary, i.e. fractionation of I and II on the one hand, and of formic acid, a small amount of water where relevant, and II on the other hand. However, these additional separation operations do not present any difficulties and have virtually no adverse effect on the cost-efficiency of the overall process of acid recovery.

The number of theoretical separation stages (plates) depends on the particular distillation task, i.e. on the type of solvent I, and therefore cannot be generalized for all cases. As a rule, however, the number of separation stages is from 5 to 50, in general from 15 to 25.

The distillation is generally carried out under reduced pressure, the pressure being reduced just sufficiently to avoid a troublesome level of decomposition reactions resulting from elevated temperatures. A pressure lower than 40 mbar (absolute) is generally not required.

The presence of the carboxamides II permits the temperature in the middle section of the column to be substantially reduced. The lower temperatures (by about 10°–50° C.) result in lower thermal loading of the material being distilled, or permit more economical operation under relatively high pressure. Furthermore, the separation efficiency increases and the same result can therefore be achieved with a lower reflux ratio, so that the energy demand is also reduced.

EXAMPLE

Recovery of substantially anhydrous formic acid from a mixture containing N-di-n-butylformamide and a little water The experimental apparatus used was a packed column having a length of 1.3 m and an internal diameter of 4 cm. The column was filled with glass Raschig rings (diameter 3 mm) which corresponded to about 21 theoretical plates. The distillation was carried out under a top pressure of 80 mbar (absolute).

A mixture preheated to 45° C. and consisting of 65 g/h of formic acid, 2.5 g/h of water and 433.5 g/h of N-di-n-butylformamide was introduced continuously into the column at the height of the 9th theoretical plate (counted from below) over the experimental period of 96 hours; the temperature at the top of the column was 35° C., while that at the bottom was 155° C.

After a steady state had been reached, 30 g of monomethylformamide were introduced, as a single dose, at the height of the 9th theoretical plate. A reflux ratio of 1.0 gave 67.5 g/hour of 96% strength by weight aqueous formic acid, whose nitrogen content was below the detection limit of 20 ppm.

The bottom product comprised 432.5 g/h of N-di-n-butylformamide in which formic acid and monomethylformamide could no longer be detected.

In a comparative experiment without the concomitant use of a carboxamide II, the reflux ratio had to be increased to 1.5 for the same bottom temperature (155° C.). In spite of the greater amount of energy required as a result, the bottom product still contained 0.5% by weight of formic acid.

This result confirms that the presence of a small amount of a carboxamide II enables complete recovery of formic acid and at the same time reduces the energy demand by about 20%. Furthermore, no decomposition of the formic acid is observed when the distillation is carried out using a carboxamide II.

We claim:

1. In a process for the recovery of formic acid, by distillation from its mixture with a solvent of the formula

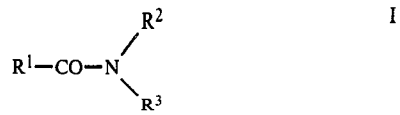

where $R^1$ is hydrogen, methyl, ethyl or vinyl and $R^2$ and $R^3$ are each alkyl, cycloalkyl, aryl or aralkyl, or $R^2$ and $R^3$ together form a 1,4- or 1,5-alkylene group, in each case of not more than 8 carbon atoms, with the proviso that the sum of the number of carbon atoms in $R^2$ and $R^3$ is 7 to 14 and that only one of these radicals is aryl, the improvement which comprises:
  carrying out the distillation in the presence of a carboxamide II which is selected from the group consisting of formamide, acetamide, propionamide and the same compounds substituted by N-methyl or N,N-dimethyl, and which has a boiling point lower than that of the solvent I.

2. A process as claimed in claim 1, wherein the solvent I is N-di-n-butylformamide.

3. A process as claimed in claim 2 using methylformamide as the carboxamide II.

4. A process as claimed in claim 1, wherein the solvent I is di-n-pentylformamide.

5. A process as claimed in claim 1, wherein the carboxamide II is selected from the group consisting of formamide, acetamide, methylformamide, dimethylformamide and N,N-dimethylacetamide.

6. A process as claimed in claim 1 wherein the amount of the carboxamide II is chosen so as to remain predominantly in the middle section of the distillation during steady state operation.

7. A process as claimed in claim 1 wherein the boiling point of the carboxamide II under atmospheric pressure is about 20°–80° C. lower than that of the solvent I and about 50°–120° C. higher than that of the formic acid.

8. A process as claimed in claim 7 wherein the difference in boiling points between solvent I and formic acid is about 100°–170° C.

9. A process as claimed in claim 7 wherein the carboxamide II is selected from the group consisting of formamide, acetamide, methylformamide, dimethylformamide and N,N-dimethylacetamide.

10. A process as claimed in claim 9 wherein the amount of the carboxamide II is chosen so as to remain predominantly in the middle section of the distillation during steady state operation.

* * * * *